United States Patent
Loeffelholz

(10) Patent No.: US 10,060,844 B2
(45) Date of Patent: Aug. 28, 2018

(54) PRESSURE RESPONSE METHOD FOR DETERMINING PROPERTIES OF SPECIES-DEPENDENT LEAKAGES IN GAS PROCESSING EQUIPMENT

(71) Applicant: HONEYWELL INTERNATIONAL INC., Morris Plains, NJ (US)

(72) Inventor: David Loeffelholz, Long Beach, CA (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 201 days.

(21) Appl. No.: 15/161,980

(22) Filed: May 23, 2016

(65) Prior Publication Data

US 2017/0336314 A1    Nov. 23, 2017

(51) Int. Cl.
    *G01N 15/08*    (2006.01)
(52) U.S. Cl.
    CPC ..... *G01N 15/0806* (2013.01); *G01N 15/0826* (2013.01); *G01N 2015/086* (2013.01)
(58) Field of Classification Search
    CPC .......... G01N 15/0806; G01N 15/0826; G01N 2015/086
    See application file for complete search history.

(56) References Cited

U.S. PATENT DOCUMENTS

| 3,561,254 | A | * | 2/1971 | Argaud et al. | ......... | G01N 15/08 73/38 |
| 3,590,634 | A | * | 7/1971 | Pasternak | ............. | G01N 15/08 374/54 |
| 3,757,947 | A | * | 9/1973 | Wakefield | ............. | B01D 61/28 210/240 |
| 4,198,853 | A | * | 4/1980 | Graham | ............. | G01N 15/0826 73/159 |
| 4,385,517 | A | * | 5/1983 | Sorce | ................. | G01N 15/0826 73/38 |
| 4,651,557 | A | * | 3/1987 | Cholet | ............... | G01N 15/0826 700/168 |
| 4,656,865 | A | * | 4/1987 | Callan | .................... | G01N 15/08 73/38 |

(Continued)

OTHER PUBLICATIONS

D. W. Bennion et al., A Sinusoidal Pressure Response Method for Determining the Properties of a Porous Medium and Its In-Situ Fluid, The Canadian Journal of Chemical Engineering, 55(2), Sep. 1971, pp. 113-117.

*Primary Examiner* — John Fitzgerald
(74) *Attorney, Agent, or Firm* — Shimokaji IP

(57) ABSTRACT

A system for building a gas processing apparatus includes a compressed gas source, a pressure modulator in communication with the gas source, and a chamber configured to receive a gas permeable material. The chamber is further configured with a first chamber area on one side of the material and with a second chamber area on a second side of the material. A sensor is configured to measure over time a pressure differential between the first and second chamber areas. A memory stores performance characteristic data for a plurality of gas processing apparatus. A processor converts the pressure differential to a material characteristic of the gas permeable material, and compares the material characteristic to at least one selected performance characteristic of the gas processing apparatus.

6 Claims, 2 Drawing Sheets

(56) References Cited

U.S. PATENT DOCUMENTS

| | | | | |
|---|---|---|---|---|
| 5,138,871 | A | * | 8/1992 | Retta .................... G01M 3/227 73/38 |
| 5,513,515 | A | * | 5/1996 | Mayer ................ G01N 15/0826 73/38 |
| 5,591,898 | A | * | 1/1997 | Mayer ................ G01N 15/0826 73/38 |
| 5,786,528 | A | | 7/1998 | Dileo et al. |
| 6,119,506 | A | * | 9/2000 | Gibson ............. G01N 15/0826 34/89 |
| 6,463,790 | B1 | * | 10/2002 | Chun .................... B01D 61/22 210/741 |
| 6,568,282 | B1 | | 5/2003 | Ganzi |
| 6,843,106 | B2 | * | 1/2005 | Swersey ........... G01N 15/0826 73/38 |
| 7,112,443 | B2 | * | 9/2006 | Hajduk .................. G01N 7/10 422/504 |
| 8,117,899 | B2 | * | 2/2012 | Piombini ........... G01N 15/0826 73/38 |
| 8,424,367 | B2 | * | 4/2013 | Ploehn ............... G01N 15/0826 73/38 |
| 9,021,865 | B1 | * | 5/2015 | D'Onofrio ............. G01N 11/08 73/37 |
| 2014/0260551 | A1 | | 9/2014 | Gray et al. |
| 2014/0318219 | A1 | * | 10/2014 | Hodgkinson .......... B01D 65/02 73/38 |

* cited by examiner

US 10,060,844 B2

PRESSURE RESPONSE METHOD FOR DETERMINING PROPERTIES OF SPECIES-DEPENDENT LEAKAGES IN GAS PROCESSING EQUIPMENT

BACKGROUND OF THE INVENTION

The present invention generally relates to gas processing apparatus and, more particularly, to apparatus and methods of characterizing membranes and seals to build gas processing apparatus.

In devices such as equipment built for space programs where leakage of gas is a prime consideration and may be gas species dependent—such as seals for a rotary distillation unit, or in applications where species-dependent gas leakage is part of the designed function of the equipment such as in O2/N2 membrane separators—it is important to be able to characterize the relative leakage rate(s) as a function of the applied pressures in a method that is independent from the normal operating conditions of the equipment. The characterization can enable one to design and build a membrane and/or membrane module suitable for use in the intended environments. The characterization can enable one to design and build a membrane and/or membrane module suitable for use in various environments.

In the absence of suitable characterization, one may be relegated to installing a membrane in a module, testing the module to see how the membrane performs, and then either using the membrane or discarding it. If the latter is needed, the process of installing another membrane and testing will be required. In essence, one must go through a trial-and-error process to determine which membrane for a given module construction will work.

As can be seen, there is a need for improved apparatus and methods to characterize membranes and seals to build gas processing apparatus.

SUMMARY OF THE INVENTION

In one aspect of the present invention, a system for building a gas processing apparatus comprises a compressed gas source; a pressure modulator in communication with the gas source; a chamber configured to receive a gas permeable material, wherein chamber is further configured with a first chamber area on one side of the material and with a second chamber area on a second side of the material; a sensor configured to measure over time a pressure differential between the first and second chamber areas; a memory that stores performance characteristic data for a plurality of gas processing apparatus; a processor that: converts the pressure differential to a material characteristic of the gas permeable material; and compares the material characteristic to at least one selected performance characteristic of the gas processing apparatus.

In another aspect of the present invention, a method of characterizing a material comprises providing a chamber having a known volume; placing the material in the chamber to create a first chamber area and a second chamber area; inputting, over a time, an oscillating pressure into the first chamber area; measuring pressure, over the time, in the first chamber area; measuring pressure, over the time, in the second chamber area; determining, over the time, a pressure differential between the first chamber area and the second chamber area; wherein the pressure differential is based on at least one of a phase difference and an amplitude difference; and converting the pressure differential to a material characteristic; wherein the material characteristic is one of a permeance factor and a leakage rate constant.

In yet another aspect of the present invention, a method of building a gas processing apparatus comprises providing a chamber; sequentially placing different materials in the chamber to create a sequential plurality of first chamber areas and second chamber areas; for each material and respective first chamber area and second chamber area: inputting, over a time, an oscillating pressure into the first chamber area; measuring pressure, over the time, in the first chamber area; measuring pressure, over the time, in the second chamber area; determining, over the time, a pressure differential between the first chamber area and the second chamber area; wherein the pressure differential is based on at least one of a phase difference and an amplitude difference; and converting the pressure differential to a material characteristic; wherein the material characteristic is one of a permeance factor and a leakage rate constant; and comparing at least one of the material characteristics for the different materials to at least one performance characteristic of the gas processing apparatus.

These and other features, aspects and advantages of the present invention will become better understood with reference to the following drawings, description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

Broadly, the present invention provides a method to characterize relative leakage rates by response to a modulated, often sinusoidal, pressure acting through the unit under test while in communication to a fixed volume. Based on the characterization, the present invention provides a method and apparatus to build a gas processing apparatus, such as an air separation module.

Generally, the present invention can be illustrated with an O2/N2 air separation membrane module. The module inlet can communicate with an oscillating pressure source while the flow out of all outlets is blocked. A comparison can then be made of the dynamic response of a shell side pressure to oscillations in a feed pressure. An amplitude attenuation and a phase difference between the two oscillating pressures are known functions of the frequency of oscillation and the total leakage coefficient (or permeance) through the membrane. For feeds with multiple gas species, correlations may be developed which map to species permeance and/or selectivity. Based on the permeance characteristics of multiple membranes, a database can be created and from which membrane(s) can be selected for building a membrane module having defined operating characteristics.

Figure 1:
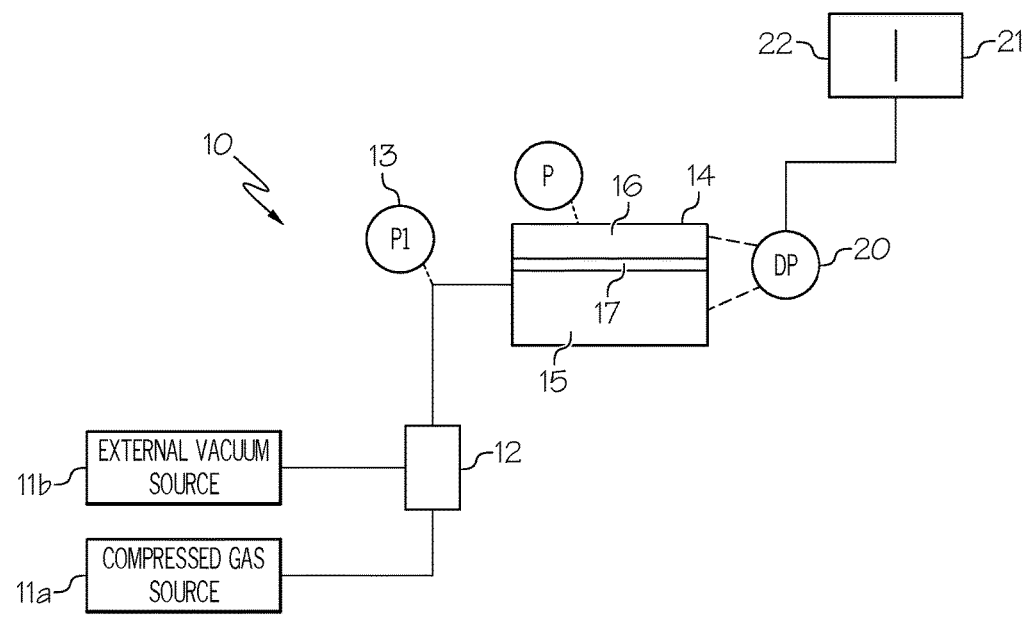
FIG. 1 is a system for building a gas processing apparatus according to an embodiment of the present invention.

FIG. 1 schematically depicts a system 10 for building a gas processing apparatus, such as an air separation module, according to an embodiment of the present invention. The system 10 may include a compressed gas source 11a and external vacuum source 11b in communication with a pressure modulator 12 which, in combination, can provide a modulating pressure 13, such as an oscillating pressure that may be in the form of a sinusoidal wave.

The system 10 may further include a chamber 14 having a known volume and configured to hold therein a gas permeable material 17, such as a membrane or seal. The gas permeable material can divide the chamber 14 into a first chamber area 15 and a second chamber area 16. The first chamber area 15 can continuously or intermittently receive the modulating pressure 13 (or P1) over a period of time. Concurrently, the second chamber area 16 can receive over the period of time leaked pressure P coming from the first chamber area 14 and through the gas permeable material 17.

Figure 2:
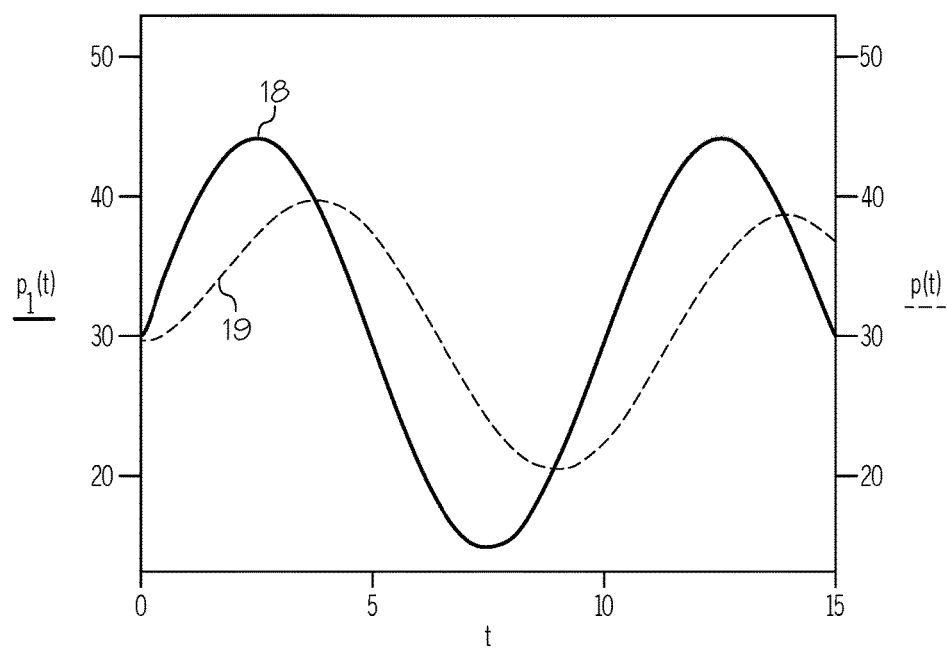
FIG. 2 is a graph of measured pressure according to an embodiment of the present invention.

FIG. 2 graphically depicts an exemplary measurement of P1 and P over time. It can be seen that in this example the modulating pressure P1 is characterized by a sine wave 18. Also, in this example, the leaked pressure P is characterized by a sine wave 19 but the phase differs from P1 (i.e., P has changed or shifted in time when compared to P1). In this example, P also differs from P1 in amplitude (i.e., P has changed or decreased in amplitude when compared to P1).

Referring back to FIG. 1, a pressure sensor 20 in the system 10 may sense and measure, over the period of time, the pressures in the first and second chamber areas 15, 16. The measured pressure data may be stored in a memory or database 21 of a computer.

A processor 22 may access the database 21 to convert the measured pressure data to pressure differential data (e.g., phase shift and/or amplitude change). Then, the pressure differential data may be converted to material characteristic data of the particular gas permeable material 17 in the chamber 14. The latter may be, for example, permeance characteristic data and/or leakage rate characteristic data of the. The material characteristic data can be stored in the database 21 or a separate database.

In an exemplary embodiment, the conversion of pressure differential data may be converted to material characteristic data as follows:

$$p_1(t) = p_0(\gamma + \beta \sin(\omega t))$$

Wherein $p_1(t)$ is the characteristic of an applied pressure signal, where $p_0$ represents initial pressure at equilibrium; $p_0(\gamma+\beta)$ represents the maximum instantaneous pressure; co is the frequency of the applied oscillation and $\beta$ is the amplitude of the oscillation with the understanding that $\gamma>0$ and $\gamma>\beta$. A material balance over a control volume in the second chamber gives a closed form solution for the pressure expected therein, which can be represented by the following equation:

$$p(t) = p_0 e^{-\alpha t} + \gamma p_0 (1 - e^{-\alpha t}) + \frac{\beta \alpha \omega}{\alpha^2 + \omega^2} p_0 \left[ \frac{\alpha}{\omega} \sin(\omega t) - \cos(\omega t) + e^{-\alpha t} \right]$$

where $\alpha$ is the ratio of leakage flux to chamber pressure corrected for temperature and chamber volume. When sufficient time has passed to establish a stable oscillatory response, a stable phase shift is observable and can be found to have the magnitude:

$$\text{phase shift} \cong \frac{1}{\omega} \operatorname{atan}(\omega/\alpha)$$

Similarly, when a sufficient time has passed amplitude ratio can also be established:

$$\text{amplitude ratio} \cong \frac{1 + \dfrac{\beta}{\gamma \sqrt{1 + (\omega/\alpha)^2}}}{1 + \beta/\gamma}$$

Both phase shift and amplitude ratio are functions of $\alpha$.

Figure 3:
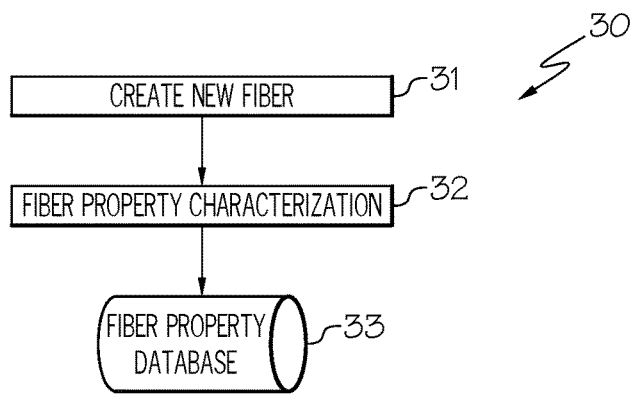
FIG. 3 is a flow chart of a method of building a database according to an embodiment of the present invention.

As depicted in FIG. 3, it can be appreciated that the present invention provides a method 30 of building, such as by the use of the system 10, a database 33 of material characteristic data, such as mass transfer coefficients, permeance and/or leakage rate characteristic data, for a plurality of gas permeable materials. In embodiments, a plurality of gas permeable materials may be collected and/or created in a step 31, wherein the materials may differ from one another based on a combination of different factors such as fiber geometry and fiber composition. Each gas permeable material may then be characterized in a step 32, such as by permeance and/or leakage rate. All characterizations can then be stored in the database 33.

Figure 4:
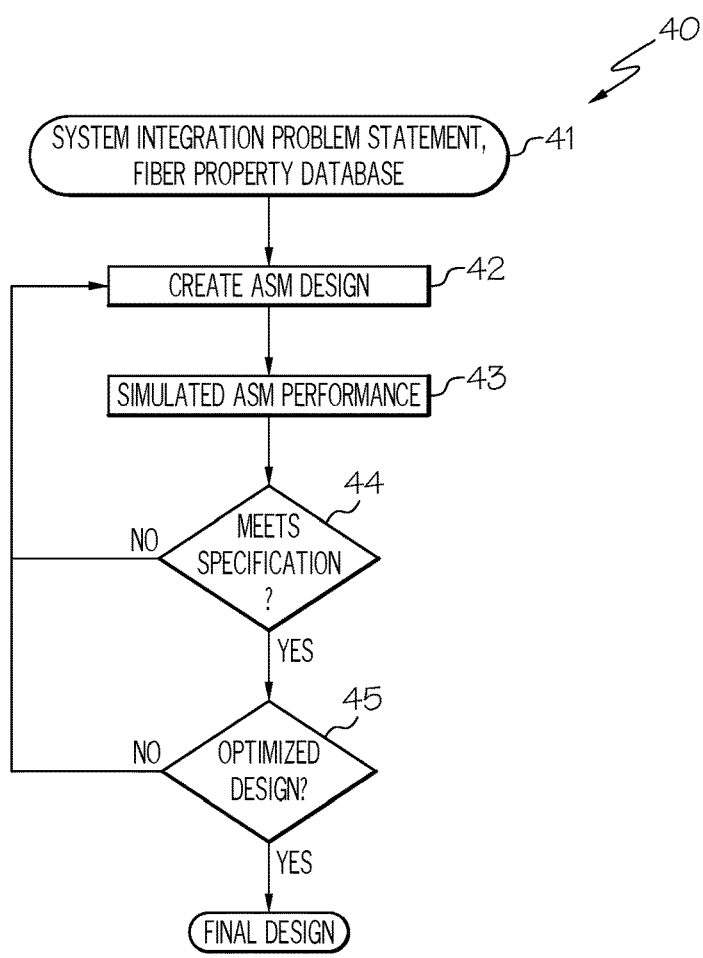
FIG. 4 is a flow chart of a method of building a gas processing apparatus according to an embodiment of the present invention.

FIG. 4 depicts an exemplary method 40 for building a gas processing apparatus, such as an air separation module which can be, for example, an O2/N2 module. In a step 41, gas processing apparatus performance characteristic(s) may be added to the database 33 or to a separate database. The performance characteristics can relate to how the gas processing apparatus is needed to perform for a particular application. Therefore, the apparatus performance characteristics may include parameters such as gas flow rates, composition of gas streams, pressure drops, etc.

In a step 42, at least one gas permeable material characteristic may be compared, such as by the processor 22, to at least one selected gas permeable apparatus performance characteristic. Based on comparative similarity(s), a computer simulated gas processing apparatus can be designed, such as by the processor 22. The design parameters can include parameters such as interfacial area, maximum and minimum working pressures, equipment geometry, and other application specific parameters.

In a step 43, the computer simulated apparatus design may undergo computer simulated operation, such as by the processor 22, during, for example, steady-state operation.

In a step 44, it can be determined, such as by the processor 22, whether the simulated operation met at least one of the apparatus performance characteristics. If "no", then the method 40 can return to step 42. If "yes", then the method can proceed to a step 45.

In a step 45, it can be determined, such as by the processor 22, whether the computer designed apparatus should be optimized. If "yes", then the method 40 can return to step 42. If "no", then the computer designed apparatus is converted, such as by the processor 22, into a final design of an actual gas processing apparatus.

It should be understood, of course, that the foregoing relates to exemplary embodiments of the invention and that modifications may be made without departing from the spirit and scope of the invention as set forth in the following claims.

I claim:

1. A method of building a gas processing apparatus, comprising:
   providing a chamber;
   sequentially placing different materials in the chamber to create a sequential plurality of first chamber areas and second chamber areas;
   for each material and respective first chamber area and second chamber area:
      inputting, over a time, an oscillating pressure into the first chamber area;
      measuring pressure, over the time, in the first chamber area;
      measuring pressure, over the time, in the second chamber area;
      determining, over the time, a pressure differential between the first chamber area and the second chamber area;
      wherein the pressure differential is based on at least one of a phase difference and an amplitude difference; and
      converting the pressure differential to a material characteristic;
      wherein the material characteristic is one of a permeance factor and a leakage rate constant;
   comparing at least one of the material characteristics for the different materials to at least one performance characteristic of the gas processing apparatus.

2. The method of claim 1, further comprising creating a database of pressure differential data.

3. The method of claim 1, further comprising creating a database of performance characteristic data.

4. The method of claim 1, further comprising designing a computer simulated gas permeable apparatus based on the material characteristic.

5. The method of claim 4, further comprising placing the computer simulated gas permeable apparatus in a computer simulated operation.

6. The method of claim 5, further comprising determining whether the computer simulated operation meets at least one apparatus performance characteristic.

* * * * *